US00PP31589P3

(12) United States Plant Patent
Kleynhans

(10) Patent No.: US PP31,589 P3
(45) Date of Patent: Mar. 24, 2020

(54) ***LACHENALIA* JACQ. F. EX MURRAY PLANT NAMED 'CHERISE'**

(50) Latin Name: ***Lachenalia* Jacq. f. ex murray**
Varietal Denomination: Cherise

(71) Applicant: AGRICULTURAL RESEARCH COUNCIL, Pretoria (ZA)

(72) Inventor: Riana Kleynhans, Benoni (ZA)

(73) Assignee: Agricultural Research Council, Pretoria (ZA)

( * ) Notice: Subject to any disclaimer, the term of this patent is extended or adjusted under 35 U.S.C. 154(b) by 0 days.

(21) Appl. No.: 14/756,801

(22) Filed: Oct. 15, 2015

(65) Prior Publication Data

US 2017/0112035 P1 Apr. 20, 2017

(51) Int. Cl.
*A01H 5/02* (2018.01)
*A01H 6/12* (2018.01)

(52) U.S. Cl.
USPC ..... Plt./263.1
CPC ..... *A01H 6/12* (2018.05)

(58) Field of Classification Search
USPC ..... Plt./263.1
See application file for complete search history.

(56) References Cited

PUBLICATIONS

UPOV hit on *Lachenalia* plant named 'Cherise', ZA PBR ZA20104393, published 2010.*
ARC*LNR *Lachenalia* and other Flower bulb cultivars at the ARC, R. Kleynhans and S. Venter, Jul. 2012.*
Guidelines for the conduct of tests for distinctness, homogeneity and stability *Lachenalia Jacq. f. ex Murray*, UPOV, TG/126/4, published Oct. 12, 1990, downloaded from http://www.upov.int/en/publications/tg-rom/tg126/tg_126_4.pdf on Jan. 11, 2018. (Year: 1990).*
CPVO Variety Data Sheet for Application No. 20141911, Applicant: Agricultural Research Council, Application/Filing Date Jul. 29, 2014, published Oct. 15, 2014, 1 page, Community Plant Variety Office, France.
Certificate of Grant of Plant Breeder's Right, Registration. No. ZA20104393, Applicant: ARC (Agricultural Research Council), dated Apr. 20, 2010, 1 page, Department of Agriculture Forestry and Fisheries, Republic of South Africa.
CPVO Variety Data Sheet for Application No. 20141910, Applicant: Agricultural Research Council, Application/Filing Date Jul. 29, 2014, published Dec. 15, 2014, 1 page, Community Plant Variety Office, France.
Certificate of Grant of Plant Breeder's Right, Registration No. ZA20104392, Applicant: ARC (Agricultural Research Council), dated Apr. 20, 2010, 1 page, Department of Agriculture Forestry and Fisheries, Republic of South Africa.
CPVO Variety Data Sheet for Application No. 20141912, Applicant: Agricultural Research Council, Application/Filing Date Jul. 29, 2014, published Oct. 15, 2014, 1 page, Community Plant Variety Office, France.
Certificate of Gram of Plant Breeder's Right, Registration No. ZA20104394, Applicant: ARC (Agricultural Research Council), dated Apr. 20, 2010, 1 page, Department of Agriculture Forestry and Fisheries, Republic of South Afriea.
CPVO Variety Data Sheet for Application No. 20141915, Applicant: Agricultural Research Council, Application/Filing Date Jul. 29, 2014, published Dec. 15, 2014, 1 page, Community Plant Variety Office, France.
Certificate of Grant of Plant Breeder's Right, Registration No. ZA20104396, Applicant: ARC (Agricultural Research Council), dated Apr. 20, 2010, 1 page, Department of Agriculture Forestry and Fisheries, Republic of South Africa.
CPVO Variety Data Sheet for Application No. 20141914, Applicant: Agricultural Research Council, Application/Filing Date Jul. 29, 2014, published Dec. 15, 2014, 1 page, Community Plant Variety Office, France.
Certificate of Grant of Plant Breeder's Right, Registration No. ZA20104397, Applicant: ARC (Agricultural Research Council), dated Apr. 20, 2010, 1 page, Department of Agriculture Forestry and Fisheries, Republic of South Africa.
CPVO Variety Data Sheet for Application No. 20141913, Applicant: Agricultural Research Council, Application/Filing Date Jul. 29, 2014, published Dec. 15, 2014, 1 page, Community Plant Variety Office, France.
Certificate of Grant of Plant Breeder's Right, Registration No. ZA20104395, Applicant: ARC (Agricultural Research Council), dated Apr. 20, 2010, 1 page, Department of Agriculture Forestry and Fisheries, Republic of South Africa.
Co-Pending U.S. Appl. No. 14/756,803, inventor Kleynhans, R., filed Oct. 15, 2015 (Not Published).
Co-Pending U.S. Appl. No. 14/756,802, inventor Kleynhans, R., filed Oct. 15, 2015 (Not Published).
Co-Pending U.S. Appl. No. 14/756,821, inventor Kleynhans, R., flied Oct. 19, 2015 (Not Published).
Co-Pending U.S. Appl. No. 14/756,819, inventor Kleynhans, R., filed Oct. 19, 2015 (Not Published).
Co-Pending U.S. Appl. No. 14/756,820, inventor Kleynhans, R., filed Oct. 19, 2015 (Not Published).
Niederwieser, J.G., and Vcelar, B., "Regeneration of *Lachenalia* Species from Leaf Explants," *HortScience* 25(6):684-687, American Society for Horticultural Science, United States (1990).
Slabbert, M.M., and Niederwieser, J.G., "In vitro bulblet production of *Lachenalia," Plant cell Reports* 18:620-624, Springer-Verlag, Germany (1999).

* cited by examiner

*Primary Examiner* — Anne Marie Grunberg
(74) *Attorney, Agent, or Firm* — Sterne, Kessler, Goldstein & Fox P.L.L.C.

(57) ABSTRACT

A new and distinct form of *Lachenalia* plant characterized by a bulb plant type having a spreading growth habit of a height of 15-30 centimetres (cm) and width of 10-15 cm having a cerise pink flower and green leave with maroon spots.

2 Drawing Sheets

*LACHENALIA* JACQ. F. EX MURRAY PLANT NAMED 'CHERISE'

Genus and species: *Lachenalia* Jacq. f. ex Murray.

Variety denomination: 'Cherise'.

BACKGROUND OF THE INVENTION

The present invention relates to a new and distinct cultivar of *Lachenalia*, botanically known as *Lachenalia* Jacq. f. ex Murray having the common name of Viooltjies/Cape cowslip and hereinafter referred to by its variety denomination 'Cherise'.

The variety was first cultivated in 2008 and originated by means of conventional breeding by the inventor during 2009 to 2010 at the premises of Agricultural Research Council Vegetable and Ornamental Plant Institute, Roodeplaat, Pretoria, Republic of South Africa.

Asexual reproduction of the 'Cherise' plant at the same location has shown that the unique features thereof are stable and reproduced true to type in successive generations of asexual reproduction.

SUMMARY OF THE INVENTION

The present invention constitutes a new and distinct variety of *Lachenalia* which originated from the controlled pollination between a *Lachenalia* hybrid as seed bearing parent and a *Lachenalia* hybrid as pollen parent as detailed hereinbelow.

The following traits have been repeatedly observed and are determined to be the unique characteristics, under the local evaluation conditions, of the 'Cherise' plant. These characteristics in combination distinguish 'Cherise' as a new and distinct *Lachenalia* cultivar:

1. Bulb plant type having a spreading growth habit of a height of 15-30 centimeters (cm) and width of 10-15 cm.
2. Flower color: cerise pink (RHS #52B).
3. Leaf color: green (RHS #141C) with maroon (RHS #53A) spots.

Color references are made to The R.H.S. Colour Chart, 1$^{st}$ edition, 1966, except where general color terms of ordinary significance are used or indicated otherwise.

Plants of the new *Lachenalia* variety 'Cherise' can be compared to similar denominations such as 'Robyn' and 'Rosabeth' but differs in that the flower color of 'Cherise' is cerise pink (RHS #52B) with darker pink (RHS #53C) tips compared to the red and red with green tips of 'Robyn' and 'Rosabeth' respectively.

BRIEF DESCRIPTION OF THE DRAWINGS

The first drawing illustrates the overall appearance of the 'Cherise', showing the colors as true as it is reasonably possible to obtain in colored reproductions of this type. The first drawing comprises a front perspective view of a typical 'Cherise' grown in an indoor nursery.

The second drawing illustrates the overall appearance of the 'Cherise', showing the colors as true as it is reasonably possible to obtain in colored reproductions of this type. The second drawing comprises a front perspective view of a typical 'Cherise' which is located in an outdoor setting.

DETAILED DESCRIPTION

The aforementioned drawings, following observations and measurements describe 'Cherise' grown by the inventor on behalf of Agricultural Research Council Vegetable and Ornamental Plant Institute, Roodeplaat, Pretoria, Republic of South Africa. Thereafter 'Cherise' was made subject of a South African Plant Breeders' Right application in March 2009. This application was granted in 2010 under number ZA20104393.

The plant is a late flowering cultivar and may be used for landscaping and should be planted during the month of March; indoors and in pots only. The plant should be kept at temperatures of 20-25 degrees Celsius during the day and 10-15 degrees Celsius at night. Plenty of light should be provided.

'Cherise' is a hybrid-hybrid cross containing the following *Lachenalia* species: *Lachenalia orchioides* subsp. *glaucina, Lachenalia bulbifera, Lachenalia quadricolor, Lachenalia rubida, Lachenalia aloides.*

The specific 'Cherise' parentage is as follows:

Female parent: (*L. bulbifera* x [*L. aloides* x *L. rubida*]) x ([*L. bulbifera* x *L. rubida*] x *L. bulbifera*).

This is the parenting background for 'Rupert'. The specific seedling resulting from the final cross as described here—was registered as cultivar 'Rupert' and a vegetatively propagated plant of 'Rupert' was used as female parent for 'Cherise'.

Male parent: {([*L. orchioides* x *L. bulbifera*] x [*L. orchioides* x *L. bulbifera*]) x ([*L. orichioides* x *L. rubida*] x [*L. orichioides* x *L. rubida*])} x {([*L. aloides* x *L. rubida*] x [*L. aloides* x *L. rubida*]) x ([*L. orchioides* x *L. bulbifera*] x [*L. orchioides* x *L. bulbifera*])}.

This is the parenting background for 'Eliza'. The specific seedling resulting from the final cross as described here—was registered as cultivar 'Eliza' and a vegetatively propagated plant of 'Eliza' was used as parent for 'Cherise'.

'Rupert' has purple flowers, compared to the cerise pink (RHS #52B) with darker pink (RHS #53C) tips of 'Cherise'. The flower orientation of 'Rupert' is similar to 'Cherise' but the flower tips of 'Rupert' are more spreading than those of 'Cherise'. The inflorescence of 'Rupert' is more compact than that of 'Cherise'.

'Eliza' has orange and red flowers compared to the cerise pink (RHS #52B) flower color of 'Cherise'. The flower orientation and density of 'Cherise' is similar to that of 'Eliza', but the flower tips are more spreading than that of 'Eliza'.

A specific seedling with number 2000/120/061 was selected from this cross and thereafter asexually propagated. The asexual progeny of this seedling is the cultivar 'Cherise'.

'Cherise' was originally produced sexually from a cross between the two varieties mentioned above. A specific seedling with number 2000/120/061 was selected from this cross and thereafter asexually propagated. The asexual progeny of this seedling is the cultivar 'Cherise' and was multiplied via tissue culture at the premises of Agricultural Research Council Vegetable and Ornamental Plant Institute, Roodeplaat, Pretoria, Republic of South Africa.

The following characteristics of 'Cherise' are described with reference to description of said characteristic which are comparable with the mentioned variety/ies having said similar characteristic.

Leaf: Monocolored.

| Characteristic: | Description of 'Cherise': | Variety having similar characteristics: |
|---|---|---|
| Attitude | Semi-erect | 'Romaud' |
| Length | Medium (20 cm) | 'Bontrok', 'Winsome' |
| Width | Medium (4.5 cm) | 'Rosabeth' |
| Ratio length:width | Medium (4.4:1) | 'Romaud' |
| Shape | Lanceolate | 'Rodelein' |
| Color | Green (RHS #141C) | 'Roinge' |
| Leaf color designation for lower sides of the leaf | Green (RHS #141C) | |
| Shape in cross-section | Angular | 'Robyn', 'Romelia' |
| Recurving of margin | Present | 'Romaud' |
| Undulation of margin | Present | 'Elegant', 'Leipoldt' |
| Blistering of upper side | Absent | 'Rodelein', 'Rosabeth' |
| Pubescence of upper side | Absent | 'Rodelein', 'Rosabeth' |
| Spots on upper side | Present | 'Bontrok', 'Roinge', 'Rosabeth' |
| Number of spots per leaf | Amount differs from plant to plant, no exact number of spots per leaf | |
| Color of spots on upper side | Maroon (RHS #53A) | |
| Size of spots on upper side | Medium (2-3 millimeter (mm)) | 'Robyn', 'Roinge' |
| Density of spots on upper side | Medium | 'Roinge', 'Rosabeth' |
| Intensity of color of spots on upper side | Medium | 'Rolina', 'Romelia' |
| Markings on outer side of leaf base | Absent | 'Rodelein' |

Peduncle:

| Characteristic: | Description of 'Cherise': | Variety having similar characteristics: |
|---|---|---|
| Length | Medium (20-25 cm) | 'Rosabeth' |
| Peduncle color designation | Purplish (RHS #53B) with green (RHS #141C) | |
| Spots or markings | Present | 'Bontrok', 'Rosabeth' |
| Coloration of peduncle spots | Purplish (RHS #53B) | |
| Size of spots or markings | Medium (1-2 mm) | 'Robyn' |
| Density of spots or markings | Medium, covers the peduncle: spots may be as close as 0.2 mm, but may differ | 'Robyn' |

Bud:

| Characteristic: | Description of 'Cherise': |
|---|---|
| Color | Cerise pink (RHS #52B) |

Inflorescence:

| Characteristic: | Description of 'Cherise': | Variety having similar characteristics: |
|---|---|---|
| Length | Medium (17 cm) | 'Robyn', 'Roklara' |
| Rudimentary apex | Inconspicuous | 'Rosabeth' |
| Number of flowers | Medium (30+ flowers) | 'Rolina', 'Romelia' |

Flower:

| Characteristic: | Description of 'Cherise': | Variety having similar characteristics: |
|---|---|---|
| Description of floral organs | Inflorescence containing individual tubular flowers attached with pedicels to the peduncle | |
| Predominant color: | Cerise pink (RHS #52B) | 'Leipoldt', 'Louis' |
| Intensity of predominant color: | Medium to strong | |
| Attitude: | Horizontal | 'Robyn', 'Romargo' |
| Flower length: | Long - 3.2 cm | 'Robyn', 'Romelia' |
| Pedicel: | Present | 'Romelia' |
| Length of pedicel: | Medium (2-3 mm) | 'Bontrok', 'Louis' |
| Flower diameter at apex: | Medium to large: 1.5 cm | |
| Flower diameter excluding apex: | Medium - 0.8 cm | 'Romargo', 'Romelia', 'Rosabeth' |
| Flower attitude of distal part of inner perianth segments: | Spreading | 'Rozanne' |
| Flower glossiness: | Absent | |
| Outer perianth segment: color of basal part just before opening of flower: | Red (RHS #47D of RHS color chart, 2nd edition, 1986) | |
| Outer perianth segment: color of basal part of fully opened flower | Red (RHS #47C of RHS color chart, 2nd edition, 1986) | |
| Outer perianth segment: color of apex relative to other part: | Clearly different | 'Ronette' |
| Outer perianth segment: color of apex is clearly different from other part | Yellow-brown (RHS #160B) | |
| Inner perianth segment: distinct spot in middle of apex: | Present | 'Ronette' |
| Inner perianth segment: color of margin of apex relative to other part: | Clearly different | 'Louis', 'Roinge' |
| Inner perianth segment: color of differently colored margin of apex: | Purple (RHS #61B) | 'Louis', 'Leipoldt' |
| Inner perianth segment: predominant color of exposed part (excluding differently colored margin of apex) | Red (RHS #47C of RHS color chart, 2nd edition, 1986) | |
| Length of inner perianth segment compared to outer segments | Longer | 'Roinge', 'Rosabeth' |
| Extrusion of stamens | Absent | 'Roinge', 'Rosabeth' |

-continued

| Characteristic: | Description of 'Cherise': | Variety having similar characteristics: |
|---|---|---|
| Fragrance | Absent | 'Romelia' |
| Predominant shape | Oblate | 'Romaud' |
| Time of flowering | Late - flowering time vary from July to August (Southern Hemisphere) | 'Bontrok', 'Roinge', 'Roklara' |
| Duration of flowering | Medium (±1 to 2 and a half months) | 'Rodelein', 'Roinge' |

Others:

| Characteristic: | Description of 'Cherise': |
|---|---|
| Description of the bulb including size and color of the bulb at maturity | Cream/white (color designation - RHS #159C) Size: between 1.5 to 2 cm in diameter |
| Time of leaf growth/bud burst | Starts within the first week of watering (normally March/April in Southern Hemisphere) |
| A description of any fruit and seed set | No seed or fruit |
| Timing of leaf senescence | After flowering has completed and starts to die down, the leaves start to die off (wheat color) and plant dry out (September - October in Southern Hemisphere) |

The variety is not genetically modified and has been tested to be free of Ornithogalum Mosaic Virus.

The invention claimed is:

1. A new and distinct variety of *Lachenalia* plant named 'Cherise' as illustrated and described herein.

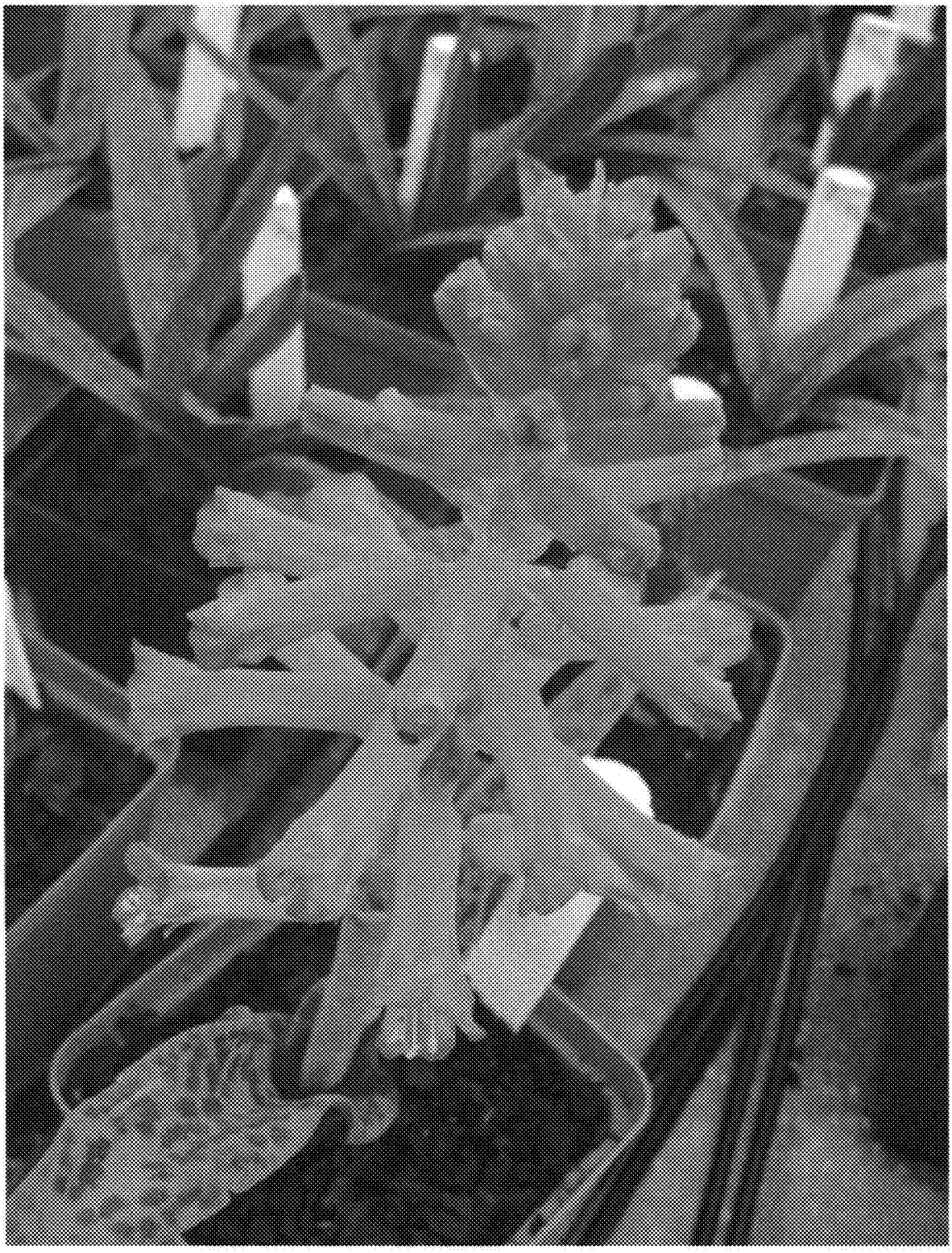

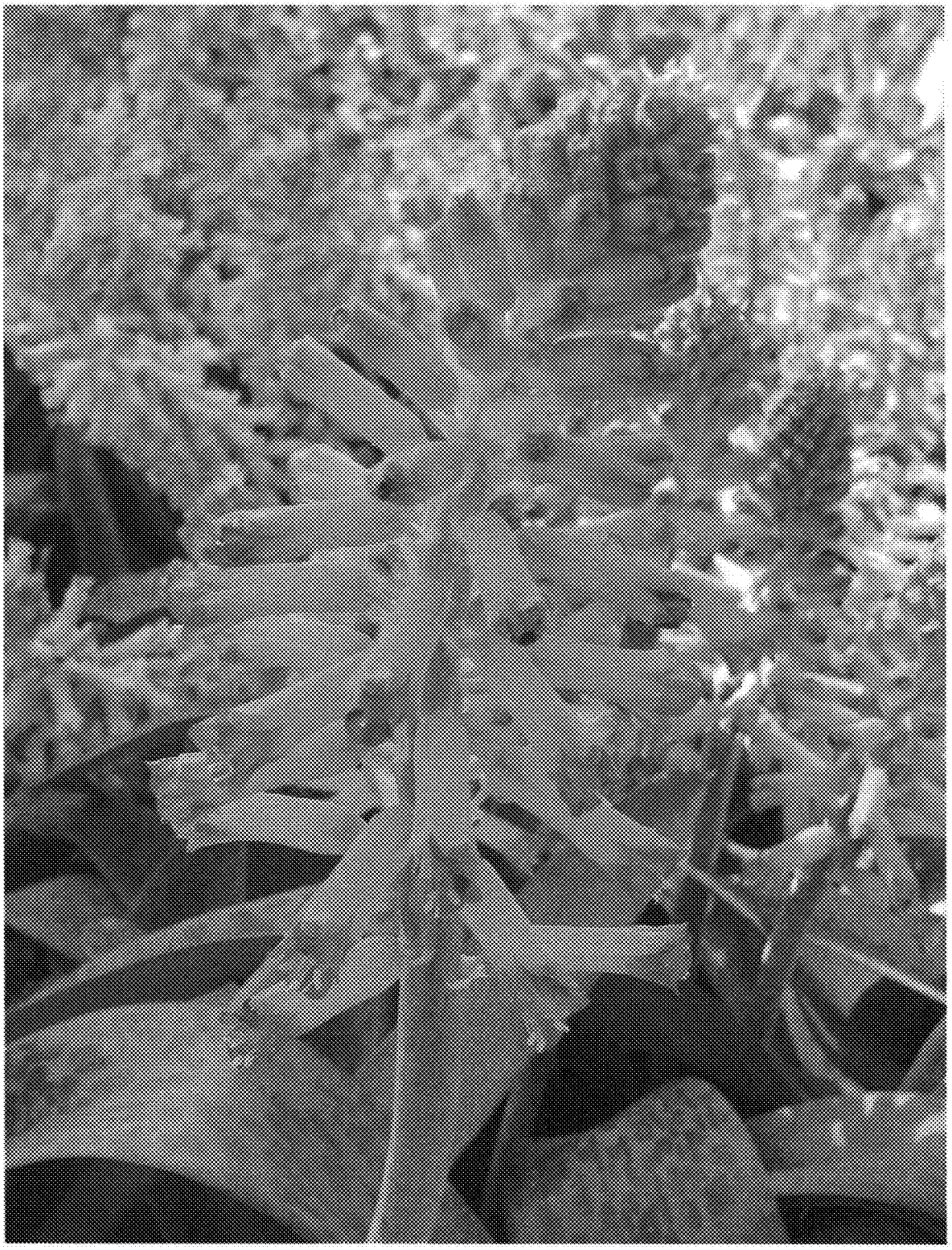

* * * * *